United States Patent
Birk et al.

(10) Patent No.: US 8,376,929 B2
(45) Date of Patent: Feb. 19, 2013

(54) IMPLANTABLE PUMP SYSTEM WITH CALIBRATION

(75) Inventors: Janel A. Birk, Oxnard, CA (US); Sean Snow, Carpinteria, CA (US)

(73) Assignee: Allergan, Inc., Irvine, CA (US)

( * ) Notice: Subject to any disclaimer, the term of this patent is extended or adjusted under 35 U.S.C. 154(b) by 772 days.

(21) Appl. No.: 12/500,464

(22) Filed: Jul. 9, 2009

(65) Prior Publication Data

US 2010/0010291 A1    Jan. 14, 2010

Related U.S. Application Data

(60) Provisional application No. 61/080,327, filed on Jul. 14, 2008, provisional application No. 61/080,956, filed on Jul. 15, 2008.

(51) Int. Cl.
*A61F 2/04*           (2006.01)
(52) U.S. Cl. ............... 600/37; 600/29; 600/30; 600/31
(58) Field of Classification Search ............ 600/29–32, 600/37; 128/897–899; 623/23.68; 604/9; 606/151
See application file for complete search history.

(56) References Cited

U.S. PATENT DOCUMENTS

| | | | |
|---|---|---|---|
| 4,157,713 A | 6/1979 | Clarey | |
| 4,592,339 A | 6/1986 | Kuzmak | |
| 4,696,288 A | 9/1987 | Kuzmak | |
| 4,760,837 A | 8/1988 | Petit | |
| 5,074,868 A | 12/1991 | Kuzmak | |
| 5,160,338 A | 11/1992 | Vincent | |
| 5,226,429 A | 7/1993 | Kuzmak | |
| 5,259,399 A | 11/1993 | Brown | |
| 5,601,604 A | 2/1997 | Vincent | |
| 5,658,298 A | 8/1997 | Vincent | |
| 5,733,257 A * | 3/1998 | Sternby | 604/27 |
| RE36,176 E | 3/1999 | Kuzmak | |
| 5,910,149 A | 6/1999 | Kuzmak | |
| 5,938,669 A | 8/1999 | Klaiber | |
| 6,210,347 B1 | 4/2001 | Forsell | |
| 6,432,040 B1 | 8/2002 | Meah | |
| 6,511,490 B2 | 1/2003 | Robert | |
| 6,547,801 B1 | 4/2003 | Dargent | |
| 6,579,301 B1 | 6/2003 | Bales | |
| 6,691,047 B1 | 2/2004 | Fredericks | |
| 6,966,875 B1 | 11/2005 | Longobardi | |
| 7,037,344 B2 | 5/2006 | Kagan | |

(Continued)

FOREIGN PATENT DOCUMENTS

EP    1 547 549 A2    6/2005
EP    1 600 183 A     11/2005

(Continued)

OTHER PUBLICATIONS

*BioEnterics Lap-Band Adjustable Gastric Banding System*, Inamed Health, pub. Aug. 28, 2003, pp. 1-115.

*Primary Examiner* — Samuel Gilbert
*Assistant Examiner* — Joshua D Lannu
(74) *Attorney, Agent, or Firm* — Linda Fox; Stephen Donovan; Debra Condino

(57) ABSTRACT

A system for facilitating obesity control includes an inflatable gastric banding device, a fluid reservoir couplable to the inflatable portion, and an implantable fluid handling device coupled to the fluid reservoir and the inflatable portion. The fluid handling device includes remotely operable components housed in a biocompatible housing. The fluid handling device includes a micropump effective to pump fluid to the band and a flow sensor. The system also includes a controller/microprocessor including an algorithm programmed to automatically calibrate the pump using data from the flow sensor, prior to adjustments made to the inflation of the gastric band.

18 Claims, 3 Drawing Sheets

| U.S. PATENT DOCUMENTS | | | | FOREIGN PATENT DOCUMENTS | | |
|---|---|---|---|---|---|---|
| 2005/0070937 A1 | 3/2005 | Jambor | | EP | 1 602 346 A1 | 12/2005 |
| 2005/0192531 A1 | 9/2005 | Birk | | EP | 1 736 123 A | 12/2006 |
| 2005/0192601 A1 | 9/2005 | Demarais | | WO | WO 01/12078 | 2/2001 |
| 2005/0250979 A1 | 11/2005 | Coe | | WO | WO 01/47575 | 7/2001 |
| 2006/0247722 A1* | 11/2006 | Maschino et al. | 607/40 | WO | WO 2005/009305 A1 | 2/2005 |
| 2007/0156013 A1* | 7/2007 | Birk | 600/37 | | | |
| 2008/0172072 A1* | 7/2008 | Pool et al. | 606/151 | | | |
| 2009/0171375 A1* | 7/2009 | Coe et al. | 606/151 | | | |

* cited by examiner

IMPLANTABLE PUMP SYSTEM WITH CALIBRATION

RELATED APPLICATIONS

This application claims the benefit of U.S. Provisional Patent Application No. 61/080,327 filed on Jul. 14, 2008, and claims the benefit of U.S. Provisional Patent Application No. 61/080,956 filed on Jul. 15, 2008, the entire disclosure of each of these applications being incorporated herein by this specific reference.

BACKGROUND

The present invention generally relates to medical devices and more specifically relates to medically implantable pumps particularly those used in conjunction with gastric banding systems for controlling obesity.

Adjustable gastric banding procedures have provided a highly effective and substantially less invasive alternative to gastric bypass surgery and other conventional surgical weight loss procedures for treating, for example, reducing or eliminating, obesity and obesity-related diseases. It has been recognized that sustained weight loss can be achieved through a laparoscopically-placed gastric band, for example, the LAP-BAND® gastric band or the LAP BAND AP® gastric band. Generally, the LAP-BAND® is placed about the cardia, or upper portion, of a patient's stomach to form a stoma that restricts the passage of food into a lower portion of the stomach. When the stoma is of an appropriate size, food held in the upper portion of the stomach provides a feeling of satiety or fullness that discourages overeating. Unlike gastric bypass procedures, laparoscopic gastric banding procedures are reversible and require no permanent modification of the gastrointestinal tract.

Over time, the stoma created by the gastric band may need adjustment in order to maintain the appropriate size which is preferably neither too restrictive nor too passive. Accordingly, the LAP-BAND® system provides a subcutaneous fluid access port connected to an expandable or inflatable portion of the band. By adding or removing fluid to or from the inflatable portion by means of a hypodermic needle inserted into the access port, the effective size of the band can be adjusted to provide a tighter or looser constriction.

Naturally, it would be desirable to allow for adjustment of the band constriction without the use of a hypodermic needle. Thus, automatically adjustable gastric banding systems as well as remotely adjustable gastric banding systems have been proposed.

Birk, U.S. Patent Application Publication No. 2007/0156013, commonly assigned herewith and incorporated in its entirety herein by this specific reference, discloses an automatically adjustable gastric band system including an adjustment assembly that includes a sensor for sensing fluid pressure in the expandable portion of a gastric band. The adjustment assembly further includes an implantable pump connected to the expandable portion, and a controller for operating the pump to allow for automatic adjustment the volume of the fluid in the band based on the sensed fluid pressure.

Birk et al. U.S. Patent Application Publication No. 2007/0265645 commonly assigned herewith and incorporated in its entirety herein by this specific reference, discloses a self-regulating gastric band adjustment assembly including an implantable fluid reservoir for containing a volume of the fluid useful for adjusting the band.

Coe, U.S. Pat. No. 7,338,433, commonly assigned herewith and incorporated in its entirety herein by this specific reference, discloses a remotely controllable gastric banding system including a pressurized reservoir with valves, and a controller for remotely controlling the valves from outside the patient.

There continues to remain a need for more effective implantable pump systems for use with adjustable gastric bands, particularly such implantable pump systems including calibration.

SUMMARY OF THE INVENTION

Accordingly, an improved remotely adjustable band (RAB) system for facilitating obesity control is provided by the present invention.

In one aspect of the invention, a system for facilitating obesity control is provided wherein the system generally comprises a gastric banding device including an inflatable portion, a fluid reservoir couplable to the inflatable portion, and an implantable fluid handling device couplable to the fluid reservoir and the inflatable portion. The implantable fluid handling device includes a pump, a first valve, a second valve and a flow measurement device. In addition, the system comprises a controller/microprocessor system in communication with the implantable fluid handling device and including an algorithm programmed to automatically calibrate the pump. The algorithm may include a calculation of an actual pump rate based on repeated measurements of pressure and flow rate during inflating or draining the inflatable portion of the band. The controller/microprocessor system includes an external or remote controller, useful for controlling the implantable fluid handling device.

In a specific embodiment, the algorithm is programmed to calibrate the pump prior to initiation of a pumping operation for adjusting volume of the inflatable portion. The algorithm may comprise a sequence of operation of the flow measurement device, the first valve, the second valve and the pump.

Between adjustments of the inflatable portion of the band, both of the first and second valves are closed. The pump may be a one-way, or uni-directional pump. The flow measurement device is capable of measuring at least one of flow rate and pressure and is capable of providing indicative signals to the microcontroller.

In another aspect of the invention, a method of adjusting a stoma size of a gastric banding patient is provided. The method generally comprises the steps of remotely commanding an adjustment of a volume of fluid in an inflatable portion of an implanted gastric band and automatically calibrating a pump in fluid communication with the inflatable portion of the gastric band. The calibration comprises initiating a sequence of operation of a pump and a pressure and/or flow sensor. In a preferred embodiment, the sequence of operation includes operation of one or more active valves during the calibration. After the calibration steps, the calibrated pump is activated to cause adjustment, more specifically, precise and reliable adjustment, to the volume of fluid in the inflatable portion of the implanted gastric band.

It can be appreciated therefore, that advantageously, a physician commanding a specific volume adjustment of the gastric band in accordance with the present invention, is assured that the actual volume adjustment (for adjusting a stoma size) reflects the requested volume adjustment, despite alterations to the pump rate over time, and despite whether the band is frequently adjusted or rarely adjusted for a particular gastric banding patient.

In some embodiments, the step of calibrating includes calculating an actual pump rate based on at least two flow parameters measured by the flow sensor. For example, the step of calibrating includes calculating an actual pump rate based on repeated measurements of pressures and flow rates. In some embodiments of the invention, such repeated measurements are made at a rate of about 25, to about 50 to about 100 or more measurements per second.

For example, the algorithm includes calibrating a pump automatically after a user, for example a physician, enters a requested volume to be pumped to a gastric band by means of a remote controller keypad. The calibration generally includes measuring initial fluid pressure in the fluid line between the pump and the band. A first valve is opened and test pump is operated (e.g. fluid is pumped to the band) for predetermined number of pump cycles. After the test pump, the first valve is closed, and a second valve is opened which allows the pumped volume of fluid to drain away from the band. During draining or immediately thereafter, a calibration loop in initiated. The calibration loop includes repeatedly measuring flow rate and pressure in the line until the pressure is substantially equal to the initial fluid pressure. The flow rate values are then used to calculate the volume of fluid drained and the actual pump rate.

Each and every feature described herein, and each and every combination of two or more of such features, is included within the scope of the present invention provided that the features included in such a combination are not mutually inconsistent.

BRIEF DESCRIPTION OF THE DRAWINGS

The present invention may be more clearly understood and certain aspects and advantages thereof better appreciated with reference to the following Detailed Description when considered with the accompanying Drawings of which.

DETAILED DESCRIPTION

Figure 1:
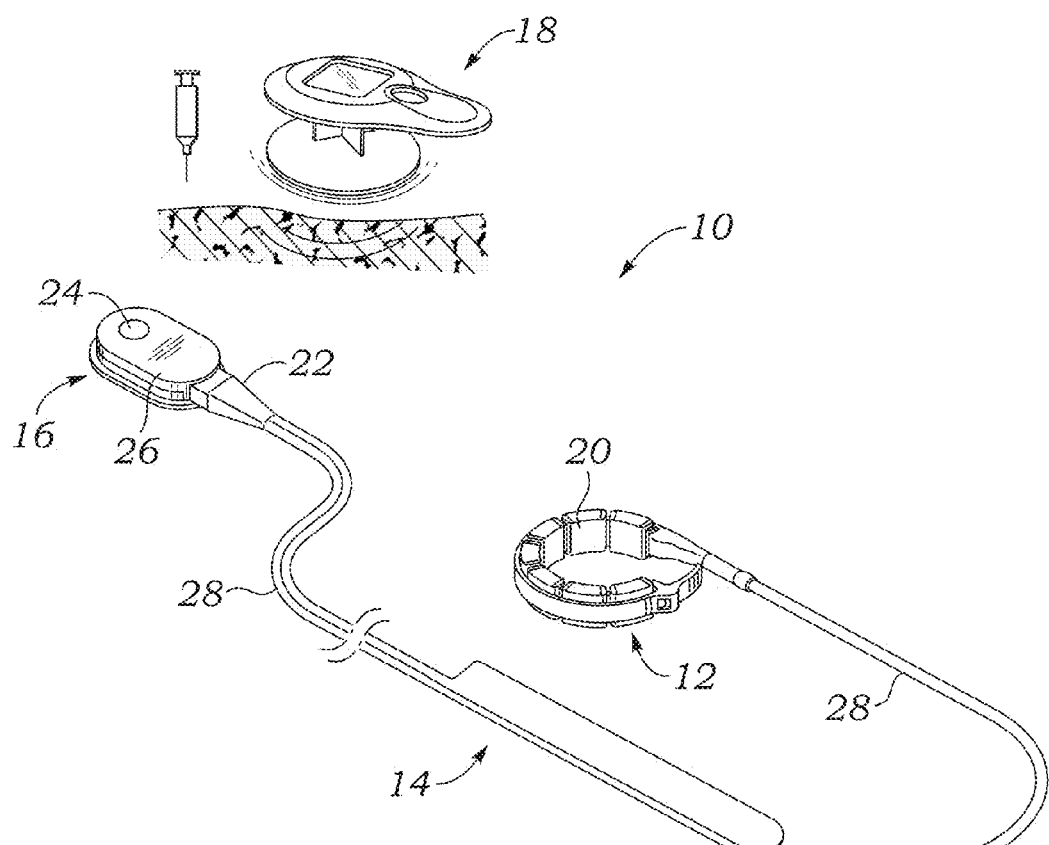
FIG. 1 is a perspective view of a gastric banding assembly including an implantable pump system in accordance with an embodiment of the invention.

Turning now to FIG. 1, an assembly 10 in accordance with the invention for controlling obesity or facilitating weight loss is shown. The assembly 10 generally includes a gastric band 12 having an inflatable portion 20, a fluid reservoir 14, an implantable fluid handling device 16, and a remote controller unit 18. The implantable fluid handling device 16 includes a connector 22 having inlet and outlet ports (not shown in FIG. 1) coupling the fluid reservoir 14 to the inflatable portion 20 of the gastric band 12. The remote controller unit 18 is configured to be in electronic communication, for example, radiofrequency communication, with the fluid handling system 16. The remote controller unit 18 is further configured to be capable of receiving input from and displaying information to a human operator thereof.

It is to be appreciated that the reservoir 14, fluid handling device 16 and remote controller unit 18 may be used to replace a conventional subcutaneous fluid access port/injection port in a conventional hydraulically adjustable gastric banding system. Helpful information regarding hydraulically adjustable gastric banding systems including subcutaneous fluid access ports/injection ports may be found in Vincent, U.S. Pat. No. 5,601,604; Kusmack U.S. Pat. No. 5,226,429; Birk, U.S. Patent Application Publication No. 2005/0192531, the disclosure of each of these patents and publications being incorporated herein in its entirety by this reference.

Surgical techniques useful for placing the present system in a gastric banding patient may be identical or similar to conventional surgical techniques used to place conventional gastric banding systems. For example, the gastric band may be placed around the stomach to form a stoma using well known laparoscopic techniques. In addition, like a conventional subcutaneous fluid access port/injection port, the present fluid handling device 16 may be sutured onto or otherwise secured to the rectus muscle sheath. The tubing from the fluid handling device 16 passes through the rectus muscle into the peritoneal cavity in the same manner as the tubing of a conventional fluid access port/injection port.

Advantageously, the system 10 of the present invention allows for a remotely controlled adjustment without needles by using the remote controller 18, or an adjustment by a needle in the override port of the fluid handling system in the event that a remote controller 18 is unavailable or if the electronics become inoperable.

In accordance with the present invention, the fluid handling device 16 is structured to move precise volumes of fluid, for example, saline, in or out of the inflatable portion of the gastric band. The fluid handling device 16 may include an override port 24, a sealed housing 26, and internal electronic components as described elsewhere herein.

The reservoir 14 may comprise a soft, collapsible silicone balloon, for example, extending along a portion of connector tubing 28. The reservoir 14 holds a reserve of fluid used to inflate the inflatable portion 20 of the gastric band 12. By moving precisely metered or measured volumes of fluid along the tubing between the reservoir 14 and the inflatable portion 20 of the gastric band 12, a stoma size of the gastric banding patient can be precisely adjusted.

Figure 2:
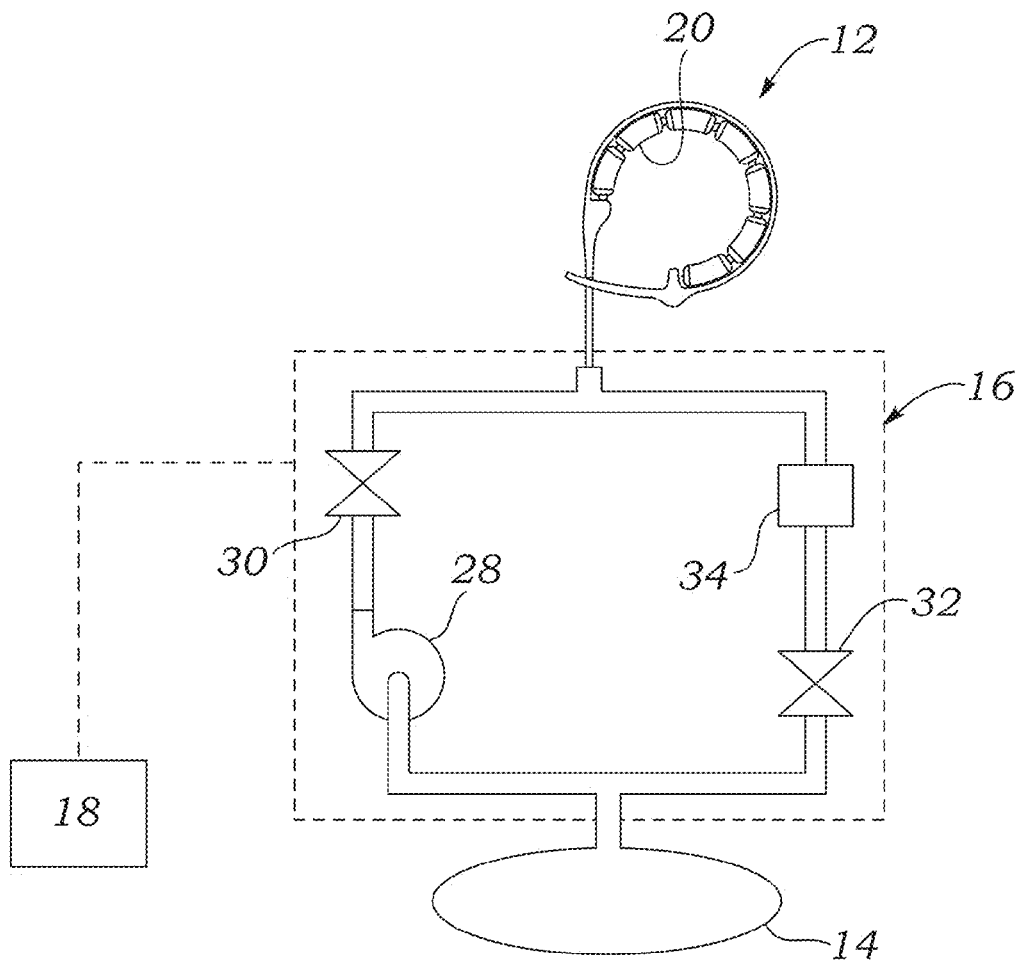
FIG. 2 is a flow diagram of the gastric banding assembly shown in FIG. 1.

FIG. 2 illustrates a fluid flow diagram of the gastric band system 10 in accordance with one embodiment of the invention. In this embodiment, the fluid handling device 16 includes a pump 28, a first valve 30, a second valve 32 and a flow measurement device 34. The components of the fluid handling device 16 are configured to operate in a cooperative manner so as to at least facilitate regulation, adjustment and/or control of inflation of the gastric band 12. Accordingly, a most desirable stoma size of a gastric banding patient can be set, maintained and even fine tuned.

The remote controller unit 18 includes a microprocessor configured to interpret command inputs from, and to provide informational data to, a human operator. In addition, the microprocessor is further configured to receive and interpret output signals, including for example pressure and/or flow rate readings, from the flow measurement device 34.

For example, the remote controller unit 18 contains electronics capable of powering and communicating with the pump 28, the first valve 30 and the second valve 32, based on operator input and/or signal output from the flow measurement device 34.

The pump 28 may comprise an electrically driven micropump, for example, an electrically driven one-way micropump, or any suitable pump useful for moving small volumes of fluid in an implanted environment, and which preferably has low power requirements and which can be remotely powered and operated. Similarly, the first and second valves 30, 32 may comprise any suitable, remotely actuatable valves known to those of skill in the art.

In an especially advantageous aspect of the invention, the system 10 further comprises means for calibrating the pump

28. Pump flow rate changes slowly over time with characteristics such as differential pressure. In order to ensure accuracy in transfer of a desired volume of fluid into or out of the inflatable portion of the band, calibration of the pump may be performed prior to each adjustment. Advantageously, this calibration may be accomplished automatically, for example, whenever a demand for adjustment is inputted into the remote controller unit 18.

The present system may include a pump calibration algorithm, for example, an algorithm programmed into the remote controller 18, which affects the sequencing and activation of the pump device, flow measurement device and valves. In some embodiments, the algorithm includes a calculation of an actual pump rate based on repeated measurements of pressure and flow rate during inflating or draining of the inflatable portion of the band.

The pump calibration algorithm is effective to compensate for variations in pump rate which may occur over time. Moreover, the pump calibration algorithm enables a high degree of precision in moving a desired volume fluid between the reservoir 14 and the inflatable portion 20 of the gastric band 12.

In a specific embodiment, the pump calibration algorithm determines the actual pump rate before initiating a pumping operation for adjusting the band. For example, a sequence of events during a volume adjustment of the band may comprise an initial test pump operation, followed by a volume measurement draining operation and ending with a calibrated pump operation.

Figure 3:
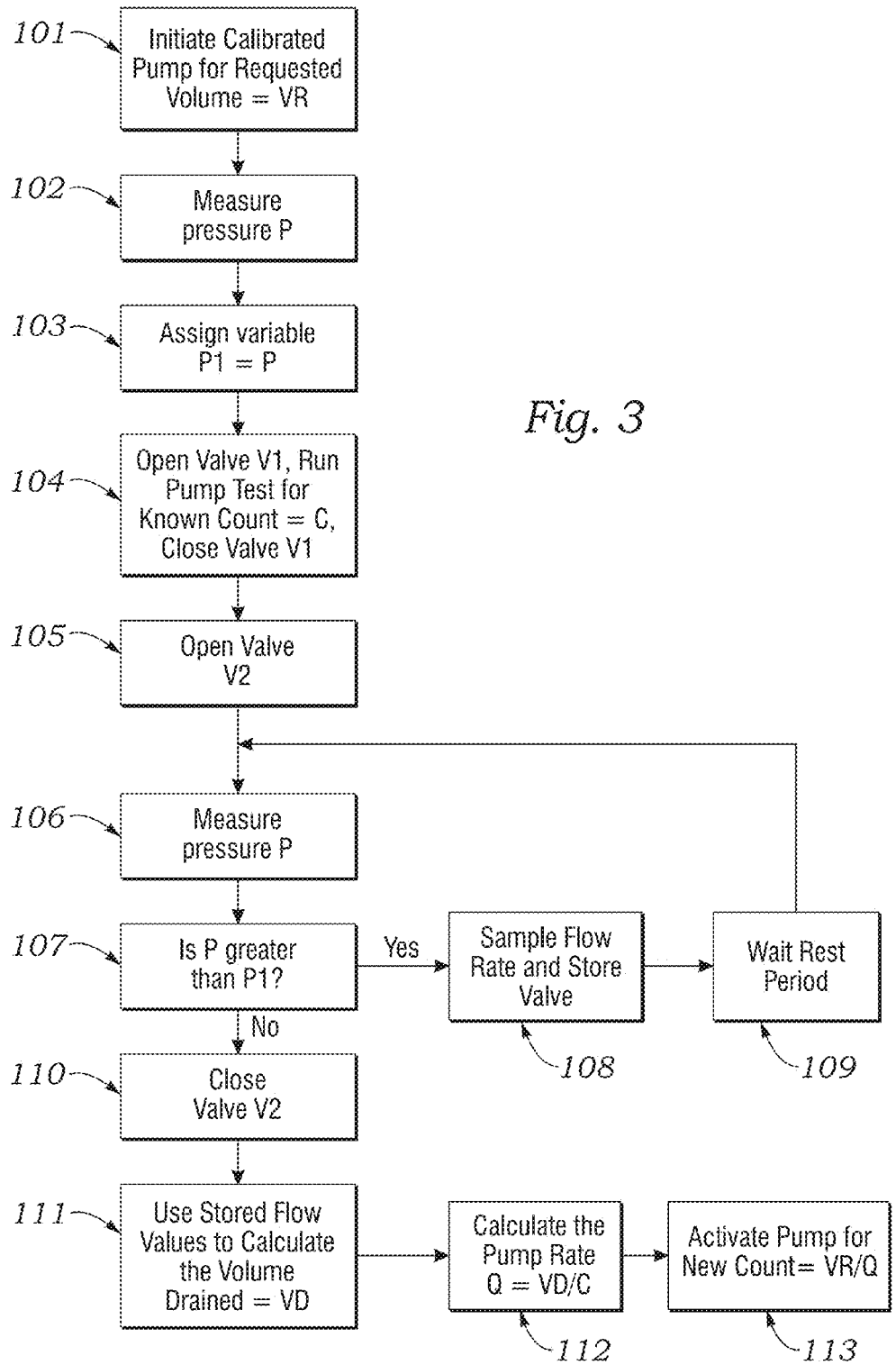
FIG. 3 is a flowchart showing an exemplary pump algorithm in accordance with an embodiment of the invention.

An example of a pump calibration algorithm sequence in accordance with an embodiment of the invention is shown in FIG. 3. Referring as well to FIGS. 1 and 2, a user, for example a physician, enters a requested volume increase, VR, e.g. VR=2.0 ml, by means of a key pad or other data entry mechanism on the remote controller 18 (101). The programmed pump calibration sequence begins by taking a pressure reading, P1, by means of a pressure sensor within the flow measurement device 34 (102). An internal counter stores this variable, P1, as a basis for later comparisons (103). The controller 18 opens first valve (V1) 30, which is in line with the pump 28, and activates the pump 28 to operate for a particular number of pump cycles C (104). The number of pump cycles may be based on at least one of a fixed number, a pressure measurement, and a requested volume measurement. For example, the number of pump cycles, C, can be determined using any combination of three parameters: for example, a fixed number (e.g., count=100 cycles), pressure (e.g., count=1.33/P1), or based on the requested volume (e.g., count=70*VR).

Once the test pump operation has completed the specified number of pump cycles, the pressure within the gastric band will have increased and the measuring flow operation can begin.

The second valve (V2) 32 in the pathway of the flow measurement device 34, is opened to allow the fluid pumped during step 104 to be drained or released back to the reservoir 105. Immediately after opening the second valve V2, pressure P is measured 106 and compared with P1 107.

If P is greater than P1, the drain cycle continues. As the drain loop (106 through 109) continues to be rerun, the flow measurement system measures the flow rate during each cycle of the loop. An optional wait period (e.g., about 10 msec) can be implemented either as a variable or constant time delay 109. This wait period can be determined to provide an overall constant sampling period or to allow other processes access to the microprocessor of the controller unit 18.

Once adequate fluid has drained from the gastric band and P is not greater than P1, the drain loop is exited and the second valve V2 is closed 110. Once flow has stopped, the algorithm calculates the volume of fluid which was drained from the gastric band 12 to the reservoir 14 (e.g., VD=1 mL) 111. One example of this calculation includes trapezoidal numerical integration of the flow data collected as a function of time. Other useful calculations will be known to those of skill in the art and are considered to be within the scope of the invention.

The pump rate, Q (e.g., about 0.001 mL/pump cycle), can then be calculated by dividing the total volume drained, VD, by the count of pump cycles commanded, C. This information is used to determine the new number of pump cycles, given by VR/Q (e.g., about 200 cycles) 113. This completes the calculation portion of the pump algorithm and now the pump device is used to move a precise amount of fluid from the reservoir to the gastric band.

In the presently described embodiment, measurement of flow rate is suspended once the second valve V2 has been closed. For a brief period of time, however, it can be expected that some additional flow may occur. An alternate embodiment of the invention which compensates for this possibility includes a second volume integration loop which continues to measure the flow rate as the valve is shutting. This second volume integration loop can be terminated either after a specified time period has been reached or after the flow being measured approaches or reaches zero.

For example, the second volume integration loop utilizes a test pumping operation, a drain measurement, and a calibrated pumping operation.

The exemplary operation sequences described herein can be modified in various ways to accomplish one or more of the objectives of the present invention. Such modified sequences will be understood by those of skill in the art and are considered to fall within the scope of the present invention.

For example, an alternative sequence of operation comprises an initial draining operation, for example, opening the second valve V2 and measuring flow rate and pressure, initiating a subsequent test pump operation for a number of pump cycles during pressure measurement to obtain a calibration, followed by pumping a calibrated volume.

It is to be appreciated that the number of pump cycles can be programmed to intentionally be less than VR or more than VR in order to optimize system speed and accuracy. For example, it is expected that there will be a tradeoff between speed and accuracy during the calibration sequence. If VR is about equal to or is less than VD, the system is likely to be operating relatively slowly but with increased accuracy. Likewise, if VR is greater than VD, the system is likely to be operating relatively more quickly but with reduced accuracy.

While this invention has been described with respect to various specific examples and embodiments, it is to be understood that the invention is not limited thereto and that it can be variously practiced within the scope of the invention.

What is claimed is:

1. A system for facilitating obesity control comprising:
a gastric banding device including an inflatable portion;
a fluid reservoir couplable to the inflatable portion;
an implantable fluid handling device couplable to the fluid reservoir and the inflatable portion, and including
  a pump;
  a first valve;
  a second valve;
  a flow measurement device; and
a controller/microprocessor system in communication with the implantable fluid handling device and configured to operate an algorithm programmed to automatically calibrate the pump with steps including:

pumping fluid from the pump through the first valve and to the inflatable portion of the gastric banding device for a predetermined number of pump cycles;

opening the second valve to allow fluid to drain from the inflatable portion of the gastric banding device;

measuring with the flow measurement device a flow rate of the fluid allowed to drain from the inflatable portion of the gastric banding device;

calculating based on the measured flow rate a volume of the fluid allowed to drain from the inflatable portion of the gastric banding device; and calculating an actual pump rate of the pump based on the calculated volume of the fluid allowed to drain from the inflatable portion of the gastric banding device and based on the predetermined number of pump cycles, the actual pump rate for use to calculate a number of pump cycles for the pump to adjust a volume of fluid in the inflatable portion of the gastric banding device.

2. The system of claim 1 wherein the controller/microprocessor system comprises an external microcontroller.

3. The system of claim 1 wherein the algorithm is programmed to calibrate the pump prior to initiation of a pumping operation for adjusting volume of the inflatable portion.

4. The system of claim 1 wherein the algorithm comprises a sequence of operation of the flow measurement device, the first valve, the second valve, the pump, and a pressure sensor.

5. The system of claim 1 wherein the pump is in line with the first valve.

6. The system of claim 1 wherein the flow measurement device is in line with the second valve.

7. The system of claim 1 wherein the pump is a one way pump.

8. The system of claim 1 wherein the pump is in parallel with the flow measurement device.

9. The system of claim 1 wherein the algorithm includes a calculation of the actual pump rate based on repeated measurements of pressure and flow rate during inflating or draining the inflatable portion.

10. The system of claim 1 further comprising a pressure sensor.

11. The system of claim 10 wherein the algorithm includes:

measuring with the pressure sensor a pressure of fluid in the inflatable portion of the gastric banding device prior to the pump pumping fluid through the first valve and to the inflatable portion of the gastric banding device for a predetermined number of pump cycles, to take a first pressure reading;

measuring with the pressure sensor a pressure of fluid in the inflatable portion of the gastric banding device after the second valve is opened to allow fluid to drain from the inflatable portion of the gastric banding device, to take a second pressure reading; and measuring with the flow measurement device the flow rate of the fluid allowed to drain from the inflatable portion of the gastric banding device until the second pressure reading is not greater than the first pressure reading.

12. A method of adjusting a stoma size of a gastric banding patient having an implanted gastric band, the method comprising the steps of:

remotely commanding an adjustment of a volume of fluid in an inflatable portion of an implanted gastric band;

calibrating a pump in fluid communication with the inflatable portion of the implanted gastric band including initiating a sequence of operation of a pump, a first valve, a second valve, and a flow measurement device, including:

pumping fluid from the pump through the first valve and to the inflatable portion of the implanted gastric band for a predetermined number of pump cycles;

opening a second valve to allow fluid to drain from the inflatable portion of the implanted gastric band;

measuring with the flow measurement device a flow rate of the fluid allowed to drain from the inflatable portion of the implanted gastric band;

calculating based on the measured flow rate a volume of the fluid allowed to drain from the inflatable portion of the implanted gastric band; and calculating an actual pump rate of the pump based on the calculated volume of the fluid allowed to drain from the inflatable portion of the implanted gastric band and based on the predetermined number of pump cycles, the actual pump rate for use to calculate a number of pump cycles for the pump to adjust a volume of fluid in the inflatable portion of the implanted gastric band; and activating the calibrated pump to cause the adjustment remotely commanded for the volume of fluid in the inflatable portion of the implanted gastric band.

13. The method of claim 12 wherein the initiating a sequence of operation includes initiating a sequence of operation of the pump, the first valve, the second valve, the flow measurement device, and a pressure sensor.

14. The method of claim 13 wherein the pressure sensor is within the flow measurement device.

15. The method of claim 12 wherein the step of calibrating includes calculating the actual pump rate based on at least two flow parameters measured by the flow measurement device.

16. The method of claim 12 wherein the step of calibrating includes calculating the actual pump rate based on measured pressures and flow rates.

17. The method of claim 12 wherein the predetermined number of pump cycles is based on at least one of a fixed number, a pressure measurement, and a requested volume measurement.

18. The method of claim 12 wherein the step of calibrating includes:

measuring a pressure of fluid in the inflatable portion of the implanted gastric band prior to the pump pumping fluid through the first valve and to the inflatable portion of the implanted gastric band for a predetermined number of pump cycles, to take a first pressure reading;

measuring a pressure of fluid in the inflatable portion of the implanted gastric band after the second valve is opened to allow fluid to drain from the inflatable portion of the implanted gastric band, to take a second pressure reading; and measuring with the flow measurement device the flow rate of the fluid allowed to drain from the inflatable portion of the implanted gastric band until the second pressure reading is not greater than the first pressure reading.

* * * * *